Figure 1:
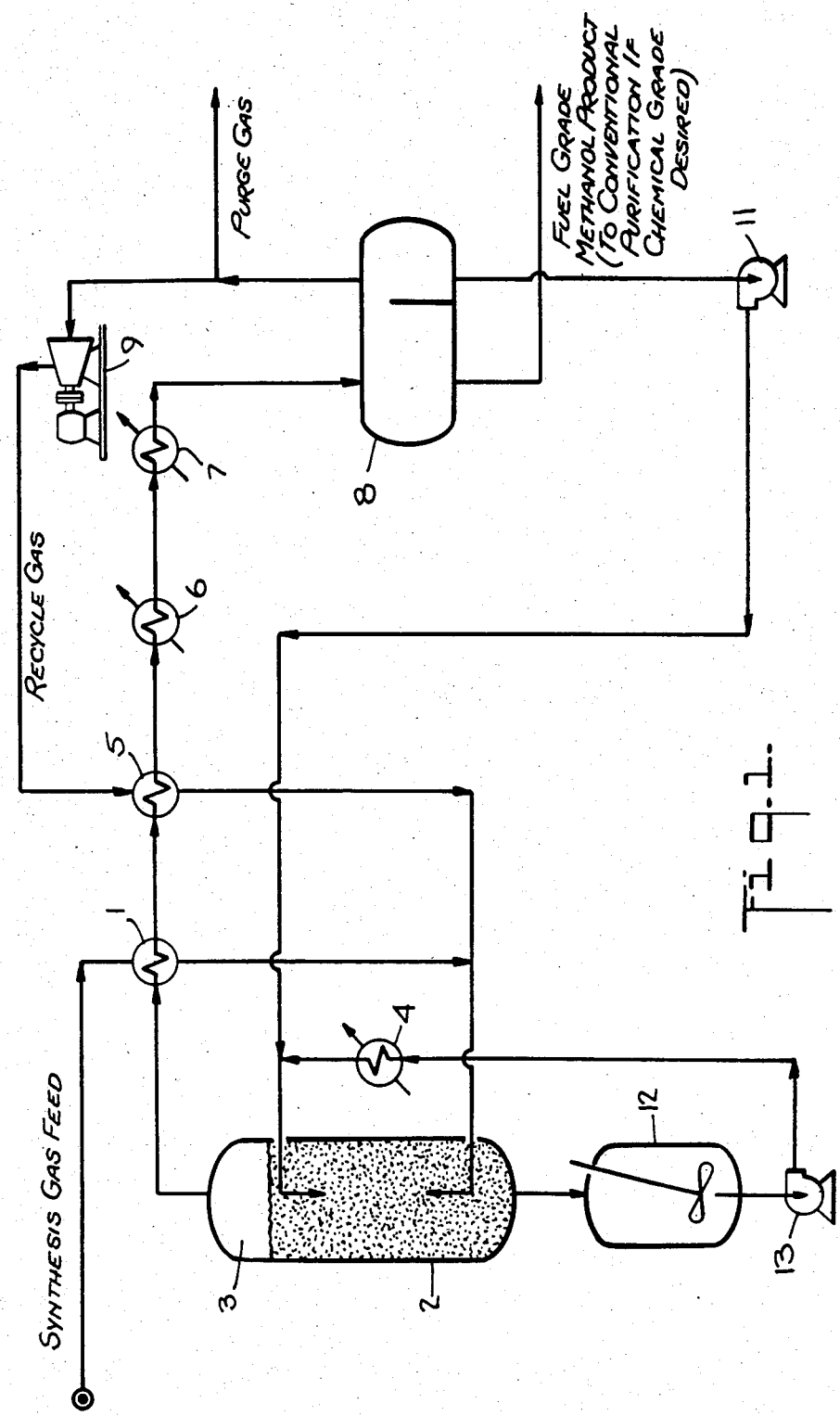

United States Patent [19]

Mednick et al.

[11] Patent Number: 4,639,470

[45] Date of Patent: * Jan. 27, 1987

[54] METHOD FOR MAKING METHANOL

[75] Inventors: R. Lawrence Mednick, Roslyn Heights, N.Y.; David B. Blum, Wayne, N.J.

[73] Assignee: Chem Systems, Inc., New York, N.Y.

[*] Notice: The portion of the term of this patent subsequent to Jan. 28, 2003 has been disclaimed.

[21] Appl. No.: 811,653

[22] Filed: Dec. 20, 1985

Related U.S. Application Data

[63] Continuation of Ser. No. 633,231, Jul. 23, 1984, Pat. No. 4,567,204, which is a continuation of Ser. No. 325,507, Nov. 27, 1981, abandoned, which is a continuation of Ser. No. 120,903, Feb. 12, 1980, abandoned.

[51] Int. Cl.$^4$ ............................................. C07C 27/06
[52] U.S. Cl. .................................................... 518/700
[58] Field of Search ......................................... 518/700

[56] References Cited

U.S. PATENT DOCUMENTS 3,888,896  6/1975  Espino et al. .
4,031,123  6/1977  Espino et al. .
4,567,204  1/1986  Mednick et al. .................... 518/700

OTHER PUBLICATIONS

Petrochemical Developments, "Make Methanol by Three Phase Reaction", 11/76, pp. 122–124.
Chem Systems Inc., Sherwin, 5/78, Abstract.

Primary Examiner—Alan Siegel
Attorney, Agent, or Firm—Bert J. Lewen; Henry Sternberg

[57] ABSTRACT

Methanol is made in a liquid-phase methanol reactor by entraining a methanol-forming catalyst in an inert liquid and contacting said entrained catalyst with a synthesis gas comprising hydrogen and carbon monoxide.

3 Claims, 3 Drawing Figures

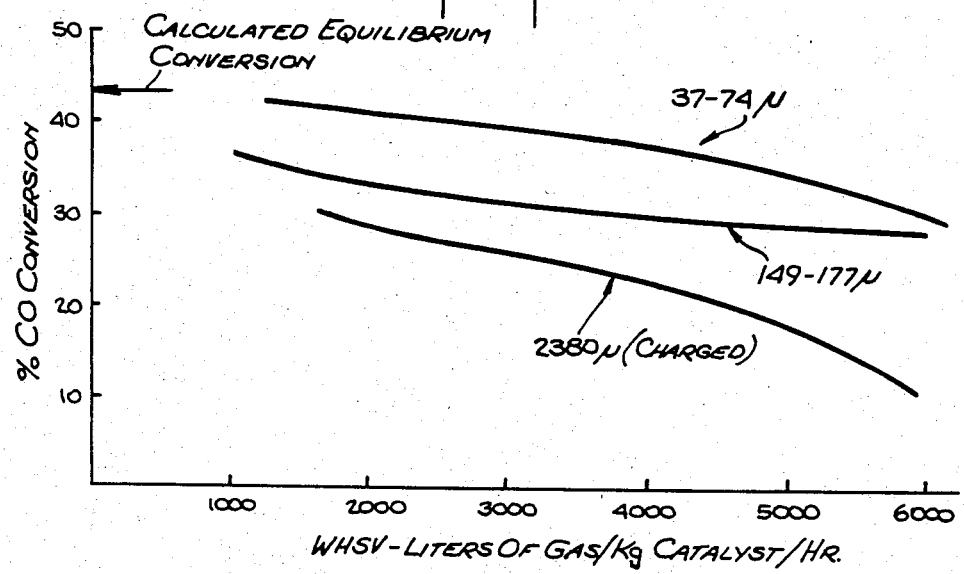
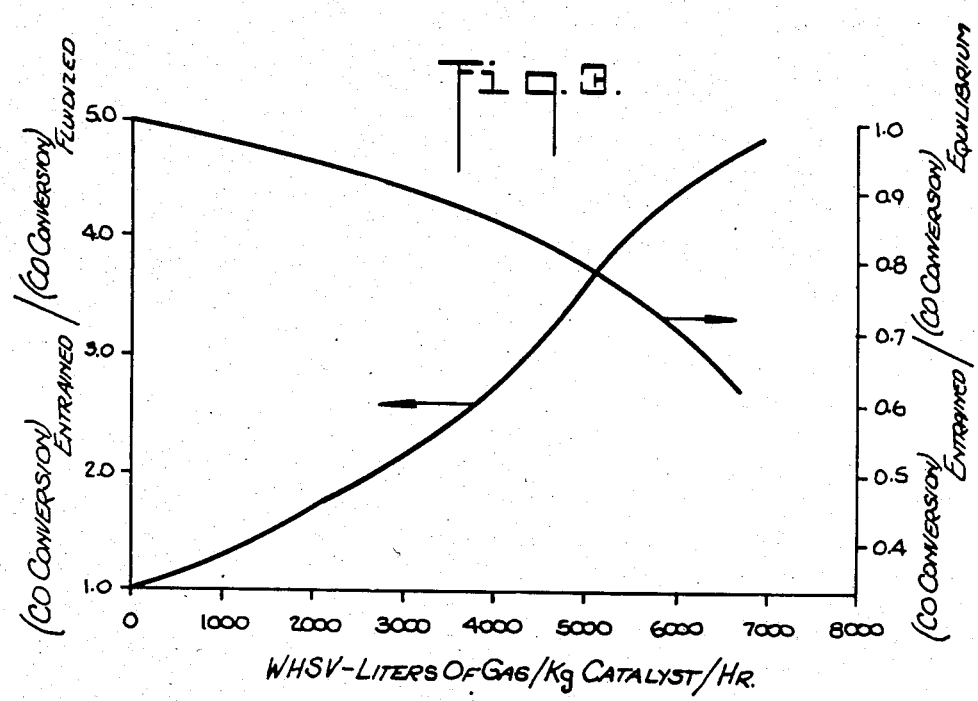

METHOD FOR MAKING METHANOL

This is a continuation of application Ser. No. 633,231 now U.S. Pat. No. 4,567,204 filed on July 23, 1984 which, in turn, is a continuation of Ser. No. 325,507 filed on Nov. 27, 1981 now abandoned which, in turn, is a continuation of Ser. No. 120,903 filed on Feb. 12, 1980 now abandoned.

This invention concerns a method for making methanol in a liquid-phase methanol reactor wherein a methanol-forming catalyst is entrained in an inert liquid and contacted with a synthesis gas comprising hydrogen and carbon monoxide.

In U.S. Pat. No. 3,888,896 to Espino et al., issued June 10, 1975, which patent is hereby incorporated by reference herein, methanol is prepared from carbon monoxide and hydrogen by saturating an inert organic liquid medium, such as pseudocumene, with the carbon monoxide and hydrogen and contacting the saturated liquid medium with a methanol-forming catalyst. Both fixed bed and fluidized bed catalysis are described. For fixed bed operation, suitable catalyst particle sizes are said to range from about 3200 to about 6400 microns whereas particle sizes of from about 200 to about 4800 microns are recommended for fluidized beds.

U.S. Pat. No. 4,031,123 to Espino et al., issued June 21, 1977, which patent is hereby incorporated by reference herein, discloses a process for forming methanol by contacting carbon monoxide, carbon dioxide and hydrogen with a bed of methanol-forming catalyst contained in a paraffinic or cycloparaffinic liquid so as to limit the concentration of the methanol in the liquid during the reaction. It is said that the catalyst bed may be fixed or slurried in, or fluidized by, the liquid. Depending upon the bed type utilized, i.e., fixed, fluidized or slurried, and the liquid flow rate employed, suitable average particle sizes are said to range from about 190 to about 6400 microns. For fluidized bed operation, the preferred particle size is said to be between 16 and 20 mesh, i.e., from about 850 to about 1000 microns.

Sherwin and Frank, in *Make Methanol by Three Phase Reaction,* Hydrocarbon Processing (November 1976), pages 122-124, describe a methanol synthesis process using an inert circulating hydrocarbon to fluidize a heterogeneous catalyst bed which controls the heat of the exothermic reaction. Catalyst activity is said to increase with decreasing particle size over the region of 1000 to 3000 microns but not in direct proportion.

Kolbel et al., in *Proc. European Syms. Chem. React. Eng.,* 3rd, Pergamon Press, Oxford (1965) at 115, report of a study regarding the hydrogenation of carbon monoxide to methane in a reactor where Ni.MgO catalyst was suspended in a paraffinic hydrocarbon. The Institute Francais due Petrole process for the hydrogenation of benzene to cyclohexane with a Raney nickel catalyst uses the cyclohexane product as a circulating liquid to carry the catalyst out the bottom of the reactor, through external heat exchangers and back into the top of the reactor. See Dufau et al., CEP, 60 (1964) at 43 and Cha et al., Oil and Gas Journal (June 10, 1974). Similar reaction systems are noted in Ostergaard, *Advances in Chemical Engineering,* Vol. 7, Academic Press, New York at 71. Most commonly, it is assumed that in systems wherein the catalyst is entrained in a liquid the catalyst remains captive within the reactor and that mixing is accomplished either by stirring or by rising gas bubbles. See Ostergaard, supra; Govindarao, Chemical Engineering Journal, 9 (1975) at 229; and Roy et al., Chemical Engineering Science, 19 (1964) at 216.

Heretofore the preferred method of liquid-phase methanol production included use of a fluidized bed catalyst, wherein a circulating inert liquid hydrocarbon and the synthesis gas feed were cocurrently introduced into the bottom of a reactor and the hydrocarbon liquid, with some assistance from the gas feed, fluidized the catalyst. In such a system, the physical limits of the reaction zone, co-extensive with the volume of the fluidized catalyst bed, are controlled principally by such factors as catalyst particle size and the velocity of the liquid hydrocarbon. The previously preferred method is not without its undesirable aspects. For example, total control of the fluidized bed requires relative uniformity of catalyst particle size, otherwise liquid velocities sufficient to fluidize large particles will carry small particles out of the desired reaction zone. Even when catalyst particles of a uniform suitable size are initially charged to the reactor, attrition of the particles, a virtually unavoidable consequence of the constant motion of particles in a fluidized bed and the inherent difficulties of producing a catalyst particle that will not be attrited in such an environment, eventually results in an undesirable distribution of particle size and the formation of catalyst fines. Entrainment of catalyst fines in the gas or liquid exiting the reactor leads to the diminution of catalyst in the fluidized bed and also creates problems in downstream process equipment. Also, the velocity of the inert liquid hydrocarbon circulating through the reactor is limited by the necessity of retaining the fluidized catalyst particles within the desired boundaries of the reaction zone. Thus the hydrocarbon liquid, which functions as a heat sink for the highly exothermic synthesis reaction, usually possesses a significant temperature gradient over the length of its passage through the reactor. Control of reaction temperature is therefore significantly hindered. A still further consequence of the relatively low liquid velocities required by the fluidized bed process lies in the necessity of cooling the hydrocarbon liquid externally of the reactor, since the poor heat transfer characteristics attributable to the low velocity preclude cooling the liquid inside the reactor, for example by means of a cooling coil.

One object of this invention is to provide a liquid phase methanol synthesis process in which the attrition of catalyst particles is virtually eliminated as a problem. A further object is to provide such a process wherein a great range of fluid velocities through the reactor may be utilized. A still further object of the invention is to provide a liquid phase methanol reaction process permitting significantly greater control over temperature profiles within the reactor.

The process of the present invention utilizes relatively small catalyst particles entrained in an inert hydrocarbon liquid as opposed to a fluidized catalyst bed in the liquid phase production of methanol. Among the advantages of the instant process are savings in catalyst costs, the availability of higher temperature operation of the reactor and improved temperature profiles within the reactor, and the use of less expensive reactors.

Catalyst costs are reduced through the combined effect of several aspects of the new entrained catalyst process as compared to the fluidized bed method. The preparation of catalyst particles for the fluidized bed liquid phase methanol production system typically requires obtaining catalyst powder and, through use of suitable binders, pelletizing the catalyst into particles of uniform size that will resist attrition. In the instant process, the catalyst may be used in the powdered form and, therefore, significant preparatory work may be avoided. As presently understood, the controlling mechanism in the liquid-phase methanol synthesis is the mass transfer of reactant across the liquid film surrounding the catalyst particles, whether the system under consideration incorporates a fluidized bed or the entrained catalyst process. Diminishing the catalyst particle size results in increasing the available surface area of catalyst, thereby decreasing the resistance to mass transfer. Thus smaller catalyst particle size leads to increased catalyst productivity per unit weight, requiring that less catalyst be charged to the reactor to reach a given production level. Also, the catalyst particles of smaller size are less susceptible to attrition, resulting in the formation of less catalyst fines and the alleviation of problems downstream of the reactor attributable thereto. Finally, the rate of catalyst replacement in the reactor is reduced with the elimination of the need to maintain catalyst pellets of a uniform size in the reactor. Attrition of pellets becomes an irrelevant consideration rather than a cause for catalyst replacement.

Higher temperature reactor conditions with the entrained catalyst system are feasible because of the higher reactivities attainable without adverse effect on methanol yields. Increased reactor operating temperatures allow recovery of the exothermic heat of reaction as higher pressure steam.

Improved temperature profiles within the reactor represent another potential benefit of the entrained catalyst process. For example, use of a countercurrent reactor configuration, which is simply not an option with the fluidized bed system, results in temperature profiles that improve CO conversion by allowing product gases to exit the reactor at the cold end of the liquid feed, thereby gaining a 20–30 C.° advantage in the thermodynamically-limited CO conversion. Also, the higher fluid velocities possible with the instant process result in improved gas-liquid heat transfer characteristics and consequently improved temperature profiles within the reactor. Higher fluid velocities also result in enhanced reaction rates since they improve gas-liquid mass transfer characteristics.

The foregoing advantages of the entrained catalyst process combine to allow the construction of less expensive, greater length-to-diameter ratio reactors for given levels of production.

In the process of the present invention, the catalyst in powdered form, preferably having a particle size of less than about 125 microns, and more preferably from about 10 to about 125 microns, is purposefully suspended in an inert hydrocarbon liquid and the catalyst entrained in the liquid is circulated through the reactor. Thus rather than being required to judiciously determine and set appropriate fluid velocities through the reactor and/or suitable catalyst pellet size in order to fix the desired boundaries of a fluidized catalyst bed, one using the liquid-entrained catalyst system of the present invention may set fluid velocities through the reactor solely on the basis of other considerations.

The ability to increase the velocity of the inert hydrocarbon liquid and entrained catalyst through the reactor provides several options not available to the practitioner of the heretofore preferred fluidized bed liquid phase methanol process. Rather than encountering a significant gradient from the inlet to outlet liquid temperatures, for example, the liquid may be circulated through the reactor at a rate great enough so that the temperature gradient of the liquid can be markedly reduced. Thus a relatively narrow optimum reactor temperature range highly favorable to equilibrium conditions may be maintained and the highly exothermic reaction may proceed under conditions approaching isothermal.

Since higher liquid velocities through the reactor significantly increase the potential for good heat transfer between the liquid and heat exchange means within the reactor itself, the liquid-entrained catalyst system permits avoidance of heat-exchange external of the reactor and allows removal of excess heat via a cooling coil in the reactor, for example. Also, since the catalyst, which preferably makes up to 5 to 40 weight percent of the liquid-catalyst mixture, provides additional heat capacity as compared to the fluidized bed system, the volumetric circulation rate of process liquid will be lower with the entrained catalyst system.

The liquid hydrocarbon employed must be capable of dissolving at least small amounts of hydrogen, carbon monoxide, and methanol; must be stable and substantially inert; and most of it must remain liquid in the reactor at the temperature and pressure employed. Naturally, the catalyst must not dissolve or react with the liquid. Generally, the vapor pressure of the liquid should not exceed 34 atm. abs. (500 psia) at a temperature of 250° C. Organic compounds are preferred.

Examples of compounds which may be used are aromatics, such as alkylated naphthalenes having 10 to 14 carbon atoms, alkylated biphenyls having 12 to 14 carbon atoms, and polyalkylbenzenes having 7 to 12 carbon atoms and 1 to 5 alkyl substitution groups (e.g., pseudocumene, xylene, and diethylbenzene); saturated alcohols having from 5 to 20 carbon atoms (e.g., cyclohexanol and n-octyl alcohol); saturated esters having from 5 to 15 carbon atoms (e.g., n-amyl acetate and ethyl n-valerate); saturated paraffins (including cycloparaffins) having 6 to 30 carbon atoms (e.g., hexane, dimethylpentane, and hexadecane); and blends of the foregoing, with paraffins and aromatics being preferred.

The reaction temperature is broadly from 100° to 500° C., preferably from 200° to 400° C., and most desirably from 215° to 275° C. Pressures of 200 to 10,000 psia, preferably from 500 to 3,500 psia, and most desirably from 500 to 1,500 psia, may be employed. The ratio of hydrogen to carbon monoxide in the feed gas is preferably from 0.6 mole of hydrogen per mole of carbon monoxide up to 10 moles per mole. Other gases, such as carbon dioxide and methane, may be present in the synthesis gas. The flow rate of reactants is broadly from 0.1 to 10 kgs of feed gas per kg of catalyst per hour and preferably from 0.3 to 5.

The liquid flow through the reactor should be sufficient to prevent excessive temperature rise, and is generally from 200 to 20,000 grams per gram-mole of methanol produced and preferably from 500 to 10,000.

The catalyst employed can be any methanol-forming catalyst active within the specified temperature range, i.e., 100° to 500° C. Methanol-forming catalysts are described in detail in the following literature references: French Patent No. 1,489,682; Shokubai (Tokyo) 1966, 8, 279–83; U.S.S.R. Patents Nos. 219,569; 264,335; 269,924; and 271,497; German Patent No. 1,300,917; Khim. Prom. Ukr. 1969 (6), 7–10; Kogyo Kagaku Zassi 1969, 72 (11), 2360–3; German Patent Publications Nos. 2,016,596; 1,930,702; 2,026,182; 2,026,165; 2,056,612; 2,165,379; and 2,154,074; Khim Ind. (Sofia) 1971, 43

(10), 440-3. The active elements of the methanol-forming catalysts which may be used include copper, zinc, aluminum, magnesium, zinc, chromium, molybdenum, uranium, tungsten, vanadium and rare earths. The low-temperature methanol catalysts, such as those described in U.S. Pat. No. 3,326,956, are especially useful. The amount of catalyst entrained in the inert liquid can vary as desired or required with from about 5 to about 40 weight percent catalyst in the inert liquid being preferred.

One version of a three-phase liquid-entrained catalyst reactor system is shown in FIG. 1. Synthesis gas feed comprising hydrogen and carbon monoxide is preheated by reactor product gas in heat exchanger 1, combined with recycle gas and fed to the bottom of reactor 2 through a series of standard orifices to distribute gas bubbles throughout the reactor. The liquid-catalyst mixture, preferably comprising approximately 5-40 weight percent methanol catalyst powder in paraffinic oil and coming from surge drum 12 by way of circulating oil pump 13 and heat exchanger 4, enters the top of reactor 2 just below the vapor disengagement zone 3. The liquid-catalyst mixture enters at a temperature of approximately 240° C. and, as it travels downward in the reactor, increases in temperature by absorbing the heat liberated in the methanol reaction. The synthesis and product gases, flowing countercurrently, are gradually cooled as they rise to the top of the reactor. The countercurrent flow of gases and liquid-catalyst has a beneficial thermodynamic effect in that the gases exiting the reactor are cooler than when the fluidized bed catalyst is used and the lower temperature favors the methanol reaction equilibrium. Because of the lower temperature the circulating oil vapor pressure will be lower than in the fluidized bed system. This decreases the load on the condensed oil return system and therefore increases the overall thermal efficiency of the process.

The liquid and entrained catalyst exit the bottom of the reactor 2 and enter an agitated surge drum 12, which prevents liquid-catalyst separation. High pressure steam can be generated from boiler feed water at heat exchanger 4 before recycle of the liquid and catalyst through the reactor. Circulation through the heat exchanger unit must be carefully controlled to prevent any buildup of solids, fouling and erosion.

The reactor product gas is cooled by first preheating synthesis gas feed at heat exchanger 1, then recycle gas at heat exchanger 5, then boiler feed water at heat exchanger 6 and is given a final cooling by air or cooling water at heat exchanger 7. Methanol and any vaporized process liquid are condensed and separated in the vapor-liquid separator 8. The methanol stream produced is suitable for fuel use directly or can be sent to a distillation system (not shown) to produce chemical grade product. Unconverted gases are recycled back to the reactor via recycle compressor 9 and heat exchanger 5.

In order to reduce or eliminate the carryover of catalyst fines from the reactor by the product gas stream, the reactor may be designed to include a disengagement zone at the top. For example, the velocity of the product gas stream at the top of the reactor could be reduced by providing an expansion zone. The larger cross-sectional area of such a zone would result in a lower flow velocity of the exiting gas within the zone and reduce the likelihood of catalyst fines being carried from the liquid by the product gas and exiting the reactor along with the product gas. Where the reactor is cylindrical in form and vertically oriented, the disengagement zone could include an expansion zone in the form of an inverted truncated cone, with the small diameter end of such a zone being of the same diameter as the reactor and located just above the upper level of liquid in the reactor and with the product gas exiting the reactor at the large diameter end of the zone.

Tests were performed with commercial calcined methanol catalyst to compare reaction rates to be reasonably expected as between use of an entrained catalyst system and use of a system relying on a fluidized bed. These different catalyst forms were approximated by use of catalyst of a particle size equivalent to that which would be used under the relevant condition. In all cases the catalyst was reduced by standard procedures in the dry state, slurried into mineral oil at 15 weight percent and then charged to an agitated stainless steel reactor. The reactor was heated to 225°-230° C. and a synthesis gas feed comprising 50% $H_2$, 25% CO, 10% $CO_2$ and 15% $CH_4$ by volume was sparged into the stirred reactor at 35 atmospheres.

The preceding tests were run for three catalyst particle size distributions: (1) 37-74 micron cut (200×400 mesh) screened from catalyst powder, (2) 149-177 micron cut (80×100 mesh) screened from crushed catalyst tablets; and (3) 2380 micron catalyst (3/32×3/32-inch tablets). The data of Table I were taken without aging the catalysts and the results are illustrated in FIG. 2, where CO conversion is plotted against weight hourly space velocity (WHSV).

TABLE I

| Particle Size As Charged (Microns) | WHSV (l/kg/hr) | Space Velocity SHSV* (cc/hr cm²) | CO Conversion (Vol. %) |
|---|---|---|---|
| 37-74 | 2000 | 3.7 | 41.0 |
|  | 3800 | 7.0 | 38.0 |
|  | 6000 | 11.0 | 31.6 |
| 149-177 | 2200 | 11.9 | 34.0 |
|  | 3700 | 20.0 | 32.0 |
|  | 5800 | 31.5 | 29.2 |
| 2380** | 2700 | 65.2 | 27.2 |
|  | 4000 | 96.7 | 24.0 |
|  | 5750 | 139.0 | 14.0 |

*Surface area, hourly space velocity (SHSV) based on total external catalyst surface area within reactor, expressed as cc gas at STP/hr/cm² catalyst area.
**Catalyst discharged was 26% as 2380 microns (3/32 × 3/32 tablets), 8% as 20 × 80 mesh and 66% finer than 80 mesh (177 microns); calculated equivalent average particle diameter is 725 microns.

As evidenced by FIG. 2, the highly preferred entrained catalyst particle size of 37-74 microns yields, at commercially practical flow rates, significantly greater CO conversion than obtained with the larger particles. Indeed, at low flow rates reactions using the catalyst particles sized from 37 to 74 microns virtually reach the calculated equilibrium conversion point.

FIG. 3 is a cross-plot of the CO conversion-WHSV relationships shown in FIG. 2. In FIG. 3, however, the conversion parameter shows the relative rate of CO conversion in the entrained catalyst mode to that of the fluidized bed mode. At low space velocity there is little discrepancy between the two reaction modes but at higher space velocities, which are commercially feasible, the entrained mode yields a CO conversion equivalent to 4 to 5 times that of the fluidized mode and therefore requires only 20-25% of the catalyst necessary for equivalent production via a fluidized bed operation.

We claim:

1. A process for preparing methanol from synthesis gas containing hydrogen and carbon monoxide comprising the steps:
   (a) entraining methanol-forming catalyst particles in an inert liquid, said catalyst particles having an average particle size of less than about 125 microns;
   (b) contacting said synthesis gas with said entrained catalyst in a reaction zone at a temperature of from 100° C. to 500° C. and at a pressure of from 200 to 10,000 psia;
   (c) withdrawing from said reaction zone the inert liquid with said entrained catalyst and cooling the same in a cooling zone;
   (d) recycling said inert liquid with said entrained catalyst particles back to said reaction zone; and
   (e) withdrawing from said reaction zone methanol and unreacted synthesis gas.

2. The process of claim 1 wherein the average particle size of the catalyst particles is from about 10 to about 125 microns.

3. The process of claim 1 wherein from about 5 to about 40 wt. % of said methanol-forming catalyst particles are entrained in said inert liquid.

* * * * *